US006878132B2

(12) United States Patent
Kipfer

(10) Patent No.: US 6,878,132 B2
(45) Date of Patent: Apr. 12, 2005

(54) DEVICE FOR ADMINISTERING AN INJECTABLE PRODUCT IN DOSES

(75) Inventor: Urs Kipfer, Lutzelfluh (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 10/107,698

(22) Filed: Mar. 27, 2002

(65) Prior Publication Data

US 2002/0107477 A1 Aug. 8, 2002

Related U.S. Application Data

(63) Continuation of application No. PCT/CH00/00506, filed on Sep. 19, 2000.

(30) Foreign Application Priority Data

Oct. 5, 1999 (DE) ........................................ 199 47 826

(51) Int. Cl.$^7$ ............................. A61M 5/00; A61M 1/00
(52) U.S. Cl. ...................................... 604/111; 604/151
(58) Field of Search ................................ 604/131, 151, 604/122, 123, 27, 30, 31, 155, 154, 65–67, 111; 128/DIG. 1, DIG. 12, DIG. 13; 600/27, 30, 31, 65–67, 131, 155

(56) References Cited

U.S. PATENT DOCUMENTS

| | | | | |
|---|---|---|---|---|
| 4,529,401 A | * | 7/1985 | Leslie et al. ................ | 604/131 |
| 5,087,245 A | * | 2/1992 | Doan .......................... | 604/67 |
| 5,266,013 A | * | 11/1993 | Aubert et al. ............... | 417/474 |
| 5,582,593 A | * | 12/1996 | Hultman ...................... | 604/65 |
| 5,764,159 A | | 6/1998 | Neftel .................... | 340/870.09 |
| 6,126,595 A | | 10/2000 | Amano et al. .............. | 600/300 |
| 6,171,276 B1 | * | 1/2001 | Lippe et al. .................. | 604/67 |
| 6,290,681 B1 | * | 9/2001 | Brown ....................... | 604/246 |
| 6,368,314 B1 | * | 4/2002 | Kipfer et al. ............... | 604/506 |
| 6,554,798 B1 | * | 4/2003 | Mann et al. ................ | 604/131 |

FOREIGN PATENT DOCUMENTS

| WO | WO 99/15214 | 4/1999 | ........... A61M/5/20 |
|---|---|---|---|
| WO | WO 00/10628 | 3/2000 | .......... A61M/5/142 |

* cited by examiner

*Primary Examiner*—Nicholas D. Lucchesi
*Assistant Examiner*—Matthew DeSanto
(74) *Attorney, Agent, or Firm*—Dorsey & Whitney LLP

(57) ABSTRACT

The present invention provides a device for administering an injectable product in doses, the device including a casing, a container accommodated by the casing, a delivering appliance for delivering the product from the container, a drive for the delivering appliance, and a means for determining a malfunction of the device, wherein a vibrator motor is accommodated by the casing, the vibrator motor being triggered by the means for determining a malfunction such that it generates a vibrating alarm signal when a malfunction is determined.

9 Claims, 3 Drawing Sheets

DEVICE FOR ADMINISTERING AN INJECTABLE PRODUCT IN DOSES

CROSS REFERENCE TO RELATED APPLICATIONS

This application is a continuation of International Patent Application PCT/CH00/00506, filed on Sep. 19, 2000, which claims priority to an earlier filed German Application Number DE 199 47 826 A1, filed on Oct. 5, 1999.

BACKGROUND

The invention relates to a device for administering an injectable product in doses.

Infusion devices, such as are used for example in diabetotherapy and such as the invention also relates to in particular, comprise at least the following components: a casing; a container, accommodated by the casing, containing the product; a delivering appliance for delivering the product from the container; and a drive means for the delivering appliance. The product is subcutaneously administered from the container through a catheter and an infusion needle connected to the catheter.

For users who administer the product themselves in the context of a treatment or for other purposes, it is generally important to be able to use their infusion device discreetly and inconspicuously. Surety in handling the device should not, however, suffer as a result. Furthermore, when the device can be comfortably and simply handled, this contributes to surety in administering the product.

SUMMARY

It is an object of the invention to provide a device for administering an injectable product in doses which can be handled securely and inconspicuously.

The invention is based on a device for administering an injectable product which comprises at least the following components: a casing; a container, accommodated by the casing, for the product; a delivering appliance for delivering the product from the container; and a drive means for the delivering appliance.

The drive means preferably comprises a drive motor. In a preferred exemplary embodiment, it further comprises a spindle drive acting on the delivering appliance. A catheter comprising an injection or infusion needle may be connected or is already connected to an outlet of the container. The container is preferably an ampoule, filled with the product, which may be inserted into a receptacle formed by the casing and which can be exchanged. The aforementioned components are preferably all accommodated in the casing, as is for example the case in known infusion pumps for diabetotherapy. This is not, however, absolutely essential for the purposes of the invention. The product is preferably a medicinal and/or cosmetic active solution, for example insulin. The delivering appliance is preferably a piston, but can also be a peristaltic pump or can be formed in another suitable way. The device is preferably constantly worn on the user's body or clothing.

The device preferably comprises a means for determining a malfunction of the device. The term malfunction is intended to relate to operations, operational conditions, function and functional conditions of the device, including departures from normal, proper or correct operations, operational conditions, function and functional conditions. Such a malfunction can be due to an occlusion or leak along or on the product's path from the container to an outlet of the injection needle. Another example of a malfunction can be based in or relate to the drive means, for example a broken or defective drive motor for the delivering appliance or a broken or defective control and/or regulating system for a drive motor. Although the drive means preferably comprises a drive motor and a control system and/or regulating system for the drive motor, a non-motorized drive for the delivery means is also conceivable, for example by means of a pressure medium or a drive spring.

The device is preferably equipped with an input means, formed for example by a keyboard or a touch screen. In principle, however, a different input appliances can be provided instead or in addition, for example a speech input. By means of the input means, the user himself in particular can bring an influence to bear on administering the product.

In accordance with the invention, a vibrator motor is accommodated by the casing. The vibrator motor may be accommodated in the casing. In principle, however, it can also be fixed externally to the casing. In both cases, the vibrator motor is arranged such that a vibrating movement of the vibrator motor can be clearly and noticeably perceived by the user. Preferably, the vibrator motor causes the whole casing or a part of the casing to vibrate.

In a first preferred function, the vibrator motor forms an alternative to an acoustic or other signal provider or, which is particularly preferred, an additional appliance for alerting. If a means for determining a malfunction of the device determines the malfunction in question, the vibrator motor emits a vibrating alarm or warning signal. In this case, a trigger for the vibrator motor is connected to the means for determining the malfunction. When the malfunction in question arises and is determined, the vibrator motor is triggered and generates the vibrating alarm signal.

A vibrating alarm signal is definitely perceived by the user himself, but not by those around him. By means of the vibrator motor, therefore, a sure and at the same time discreet i.e. inconspicuous way of alerting the user is provided. If the vibrator motor is provided in addition to another alerting appliance, for example an acoustic alerting appliance, then the vibrator motor provides a redundancy with respect to the alerting appliance. If another alerting appliance is additionally provided, for example an acoustic signal provider, then a switch is preferably provided with which the user can optionally switch off one of the alerting appliances or select one of them as the alerting appliance. Advantageously, a common trigger can be provided for a number of redundant alerting appliances. The additional expense of triggering the vibrator motor can then be avoided.

The means for determining a malfunction preferably comprises a sensor which detects an impermissibly large deviation from an ideal state. The sensor is preferably a component of a means for monitoring a pressure within the components of the device which guide the product, if the malfunction to be determined is an occlusion. The sensor for this is preferably a force sensor. In such cases, a force necessary to drive the delivering appliance is measured. Preferably, the reaction force exerted by the delivering appliance is directly measured. A force sensor is preferably also used to determine a leak. Advantageously, both an occlusion and a leak may be detected by the same force sensor.

A malfunction of a drive motor and/or a malfunction of a control and/or regulating system for a drive motor is preferably detected by means of an angular position sensor for the motor. The angular position of the control system for the drive motor which the sensor detects is not adopted as a variable, but is only used for the purpose of determining the malfunction of the drive means and triggering the vibrator motor.

The malfunction can also be an advance notice that the stored energy of an energy source for the drive means has been used up. If electrical energy is required for the drive motor, then the level of charge of a battery for the drive motor, for example, can be monitored. In this case, the vibrator motor is triggered by the trigger when the level of energy drops below a predetermined minimum energy reserve.

If the device comprises an input device, a second function of the vibrator motor in accordance with the invention is to confirm inputs which have been inputted by means of the input means. Preferably, individual vibrating signals are allocated to selected input appliances or to all the input appliances of the input means. If, for example, the user inputs an extra bolus, then the individual inputs, inputted for example via a keyboard or a touch screen, are individually confirmed by a vibration. In this function of the vibrator motor, a trigger for the vibrator motor is connected to the input means.

If the drive means comprises a control and/or regulating system for a drive motor, then the trigger for the vibrator motor is preferably formed by this control and/or regulating system.

A drive motor for the delivering appliance can at the same time also form the vibrator motor. In another, different preferred exemplary embodiment, a separate vibrator motor for one of or a combination of the functions cited is provided in addition to a drive motor.

In accordance with the invention, a third function of the vibrator motor is that it vibrates when the device is primed. This ensures that the product guiding system, from the container to the outlet of the injection or infusion needle, is smoothly and securely vented. In particular, the user does not have to shake or strike the device when priming it, so that any air bubbles from priming are definitely removed. Priming is finished when the product emerges at the injection or infusion needle. It serves to vent the product-guiding components.

In a fourth function, the vibrator motor is periodically triggered in accordance with the invention, to indicate to the user tactilely that his device is functioning normally. This can be provided in addition to—or also as an alternative to—an alerting function. The positive indication that the device is functioning normally ensures particularly sure handling.

The vibrator motor provided in accordance with the invention can fulfill one of the aforementioned four functions or any combination thereof. It preferably fulfills a number and, in one embodiment, all of the four aforementioned functions.

If the vibrator motor fulfils a number of the functions cited, a characteristic vibration can be generated for each of the functions. If attention can be drawn to a number of different malfunctions using the vibrator motor, a characteristic vibrating signal is also advantageously provided for each malfunction. The vibrating signal of a malfunction differs in particular from a periodically generated signal to confirm that the device is operating normally. On the other hand, however, signals for confirming inputs can correspond to alerting signals. An individual vibration also need not be provided for priming.

The vibrator motor advantageously exhibits a maximum length of at most 20 mm and a maximum width of at most 5 mm.

DETAILED DESCRIPTION

Figure 1:
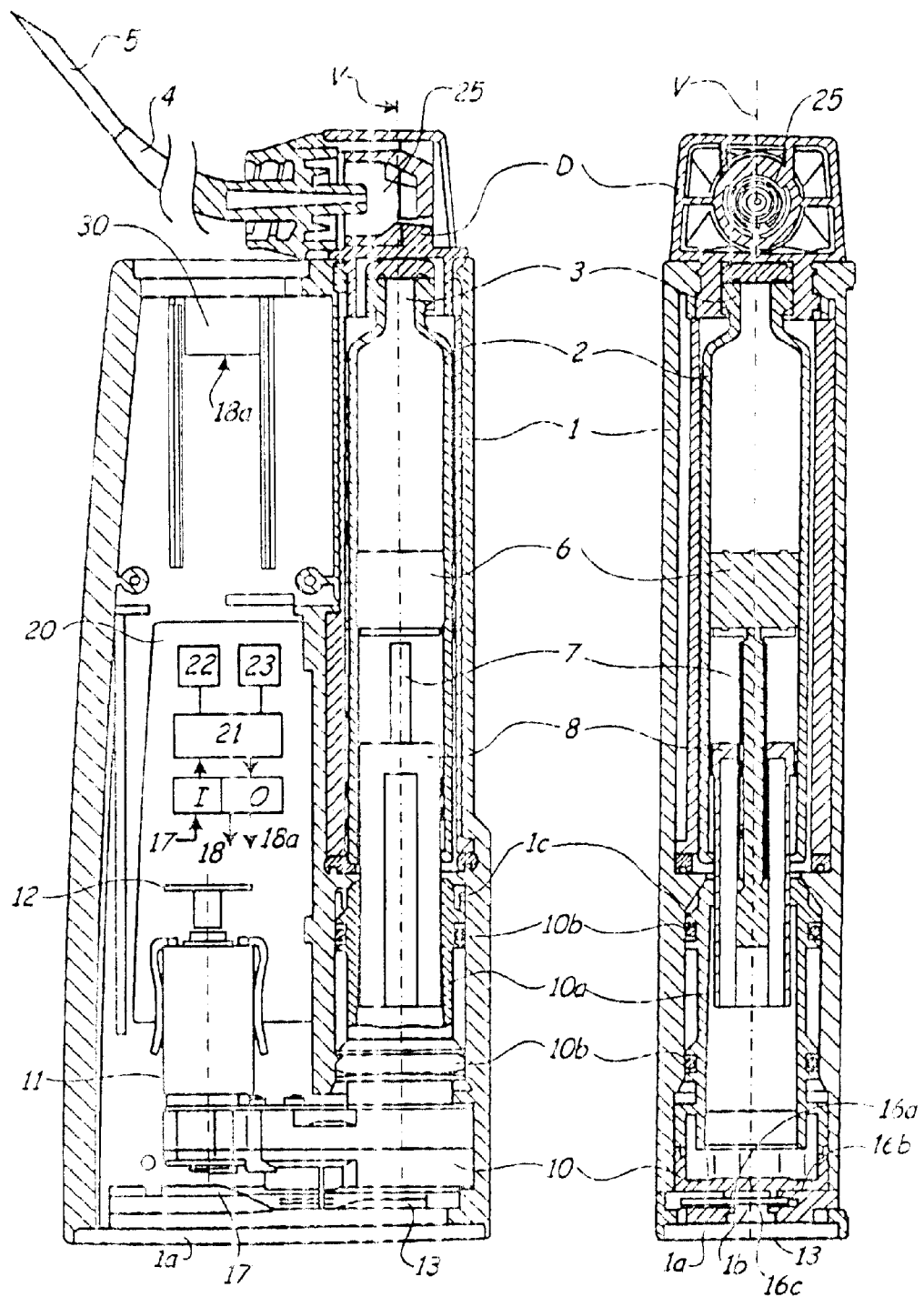
FIG. 1 is a longitudinal sectional view of an infusion pump comprising a pressure monitoring system and a vibrator motor.

FIG. 1 shows a portable infusion pump for insulin treatment. The pump, in particular its drive, is described in German patent application No. 197 17 107. Reference is additionally made to the teaching in said application, which is incorporated herein by reference.

A container in the form of an ampoule 2 is accommodated in a pump casing 1. The ampoule 2 is filled with insulin. A delivering appliance in the form of a piston 6 is accommodated in the ampoule 2 such that it is linearly slidable in a feed direction towards an outlet 3 of the ampoule. The piston 6 is advanced by a driven member 7, formed as a threaded rod, pressing on a rear surface of the piston 6. The driven member 7 is part of a spindle drive 8 which is formed with two telescopic stages. With respect to the piston drive, the invention is not however restricted to this.

When the piston 6 is advanced along an sliding axis V, insulin is delivered via a catheter 4 connected to the outlet 3 and an infusion needle 5 fixed to the front free end of the catheter 4. Together, the ampoule 2, outlet 3, catheter 4 and needle 5 may be thought of and referred to as comprising a fluid guiding system. In order to set a defined base pressure in the ampoule 2, a valve 25 is arranged on the flow path of the insulin. Such a valve can be used not only to define base pressure which continuously prevails in the fluid guiding system, but also to prevent the ampoule 2 from emptying itself under the weight of the column of fluid in the fluid guiding system. The valve 25 is preferably designed such that the ampoule is definitely prevented from undesirably emptying itself, under the conditions arising in the practical use of the infusion pump. In the exemplary embodiment, the valve 25 is accommodated in a removable casing lid D which seals an ampoule compartment after an ampoule 2 has been inserted.

The driven member 7 is driven by means of a drive motor 11, via a reduction gear, onto the spindle drive 8 comprising the driven member 7. With respect to the spindle drive and the reduction gear, reference is made to German patent application No. 197 17 107. At least the driven member 7 is guided linearly and non-rotationally in the casing 1, such that the threaded rod 7 is advanced by rotary driving two preliminary drive members of the spindle drive which surround the driven member 7 like a sleeve.

The spindle drive 8, together with the gear and the motor 11, is mounted on a sliding platform 10 which for its part is mounted as a whole in the casing 1, non-rotationally but linearly slidable in and counter to the feed direction of the piston. It would also be possible in principle to arrange the motor 11 fixed to the casing; it would be equally possible to arrange the motor 11, together with the gear, fixed to the casing. In this case, a sliding mesh—for example, a spur wheel toothing extending over a corresponding length along the feed direction—would have to be provided between the drive component fixed to the casing and the initial step of the spindle drive 8 which is then mounted on the sliding platform 10.

In order to be able to determine any malfunctions in the fluid guiding system or the components thereof, the pressure of the product fluid—in particular, for example, the fluid pressure in the ampoule 2—is monitored. To monitor the pressure, a reaction force exerted by the piston 6 on the casing 1 is measured by means of force sensor 13 and compared with a predetermined index value for the reaction force. Calibrating the index value is described in German patent application No. 198 40 992, to which reference is made in this respect and which is incorporated herein by reference.

The force exerted by the piston 6 onto the threaded rod 7 and via the spindle drive onto the sliding platform 10 and, as a result of its sliding capacity, onto the force sensor 13, is measured as the reaction force by means of the force sensor 13. For this purpose, the sliding platform 10 is mounted floating on the casing walls in the casing 1. The sliding platform 10, comprising a platform sleeve 10a, is supported, longitudinally slidably, in a part of the casing sleeve surrounding this sleeve 10a by means of elastic mounting elements 10b in the form of a pair of O-rings, for example rubber rings. The platform sleeve 10a surrounds drive members of the spindle drive formed as drive sleeves. A contact is established between the sliding platform 10 and the casing 1 only via the O-rings 10b. A sliding movement between the sliding platform 10 and the casing 1 along the sliding axis V takes place only within the context of elastic deformation of the O-rings 10b. The O-rings 10b themselves slide neither with respect to the casing 1 or with respect to the sliding platform 10, but only elastically deform. By forming this floating mounting, frictional forces are minimized and the force applied by sliding the piston 6 is transmitted as unaltered as possible onto the force sensor 13. The O-rings 10b are accommodated in circumferential grooves of the platform sleeve 10a and in this way are fixed with respect to these two opposing surfaces of the casing 1 and the platform sleeve 10a by a positive lock on the one hand and a frictional lock on the other. They could, however, also be connected in a material bond to one of these two surfaces, and if appropriately assembled they could also be pressed together between the two oppositely moving surfaces and in this way held only in a frictional lock. In any event, it should nonetheless be ensured that no other frictional forces have an effect when sliding the sliding platform 20, except the elastic deforming forces.

The force sensor 13 is arranged between a rear facing surface of the sliding platform 10 and a wall of the casing 1 opposite the rear facing surface. It is furthermore arranged in the alignment of the sliding axis V of the piston 6, such that the reaction force acting along the sliding axis V of the piston 6 acts directly on the force sensor 13. The reaction force is introduced symmetrically with respect to the sliding axis V, and therefore cannot give rise to a substantial tilting moment.

Figure 2:
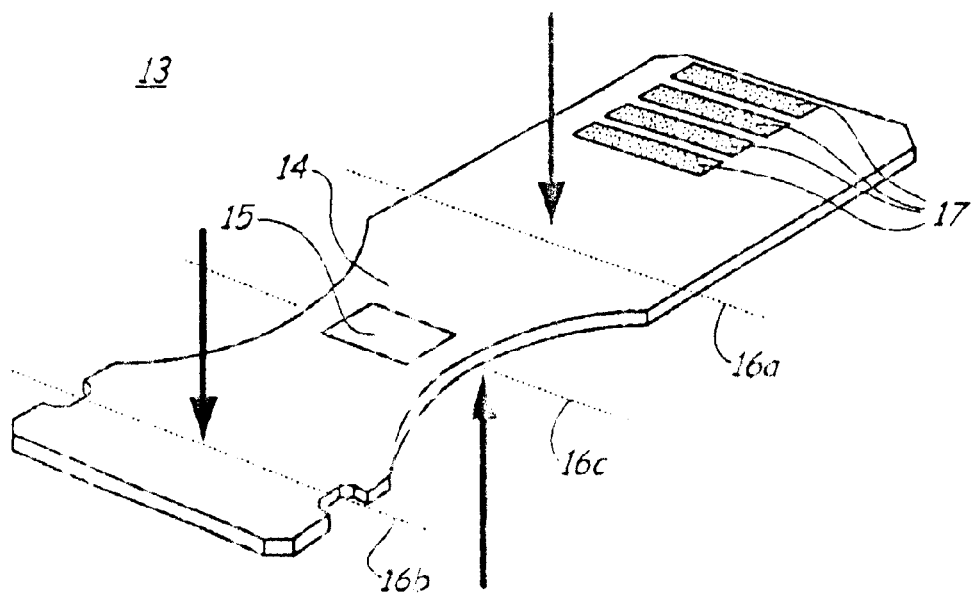
FIG. 2 depicts a force sensor for the pump according to FIG. 1.
Figure 2:
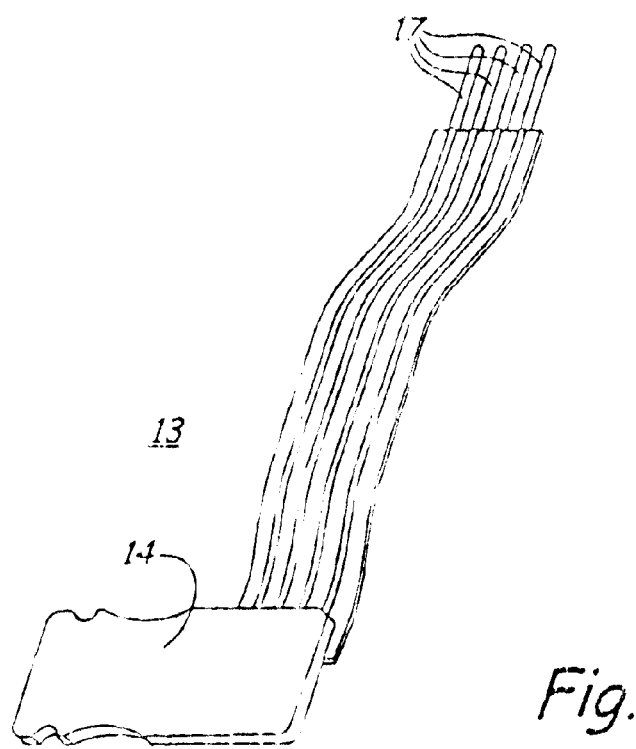

FIG. 2 shows the force sensor 13 on its own. It is formed by a bending beam 14 to which a thin-film strain measuring strip 15 is applied at least on one surface of the beam. Readings may be augmented by applying a strip to both opposing surfaces of the beam. Four lines of a bridge circuit are designated at 17. In forming the bending beam, two stays 16a and 16b (FIG. 1) are indicated as linear supports at the platform end, spaced in parallel from each other on one surface of the beam, and between which the beam 14 comprising the strain measuring strip 15 is bent by the reaction force exerted by the piston 6. To exactly define the site at which the reaction force is introduced, a further stay 16c (FIG. 1)—whose linear support is indicated in FIG. 2—projects from a base plate 1b of the under side of the casing 1 opposite the two stays 16a and 16b, exactly in the middle between these two stays 16a and 16b. The linear support of the third stay 16c lies in the alignment of the sliding axis V and parallel to the stays 16a and 16b. The three stays 16a, 16b and 16c are cross-sectionally round in the support area, such that the reaction force is introduced along the stays 16a and 16b as exactly linear as possible and the load on the support at the stay 16c also acts linearly on the bending beam 14. Other cross-sectional shapes which cause or approximate this are also suitable. Other sensors, for example piezo-resistive sensors, could equally be used instead of strain measuring strips in the context of a static measuring process.

A reading representing the impressed reaction force, preferably proportional to the reaction force, is emitted from the force sensor 13, via a line 17, to the control system 20 for the motor 11, preferably in the form of an electrical reading signal. The reading representing the reaction force currently being measured is permanently at an input I of the control system 20. The control system 20 is connected to the motor 11 via an output O and a corresponding control line or control bus 18. The motor 11 is positionally controlled.

A vibrator motor 30 is arranged in the casing 1. The vibrator motor 30 is rigidly fixed to the casing 1. In the exemplary embodiment, it is fixed in a sealing stopper of the casing 1, preferably rigidly so that the vibrations are transmitted to the casing 1. The vibrator motor 30 is connected to the output O of the control system 20 via a line 18a, i.e., it is triggered by the control system 20 via the line 18a.

If, with the aid of the force sensor 13, an occlusion is determined by the control system 20 by comparing the measured reaction force with a maximum value, then the vibrator motor 30 is triggered by the control system 20 via the line 18a and emits a characteristic vibrating signal, indicating an occlusion, via the casing 1.

The drive motor 11 is a step or stepper motor with a physically predetermined start-stop frequency. This is a frequency and a corresponding motor speed, beyond which the motor torque decreases, which cuts off the motor 11 if it experiences comparatively little resistance in this state. Once it has been cut off, it no longer starts automatically, but merely oscillates back and forth until it is completely shut off. It is then re-started by a control command from the control system 20.

The position of the motor 11 is monitored by means of an impeller 12 fixed on the axis of the motor rotor and an optical sensor co-operating with the same, for which the impeller 12 serves as a light barrier interrupter. The control system 20 shuts off the motor 11 if a control impulse does not result in the motor turning. The position of the motor is known to the control system 20, at least in the form of the number of completed revolutions from a reference position at any point in time. The position of the motor could also be ascertained by means of a counter connected to the optical sensor, which counts up the number of interruptions by the blades of the impeller 12. From this, the control system 20 also knows the position of the driven member 7 relative to the sliding platform 10, and ultimately also the position of the piston 6 in the ampoule 2.

The control system 20 comprises a micro-processor 21 having two non-volatile memories 22 and 23. A standard index value distribution S for the reaction force is stored in the memory 22. The other memory 23 is described in priming the infusion pump. The control system 20 is connected via an interface I/O to the motor 11, the force sensor 13 and other components, in particular an energy source. The connection to the force sensor 13 is indicated by the reference numeral 17 and the connection to the motor 11 by the reference numeral 18.

Figure 3:
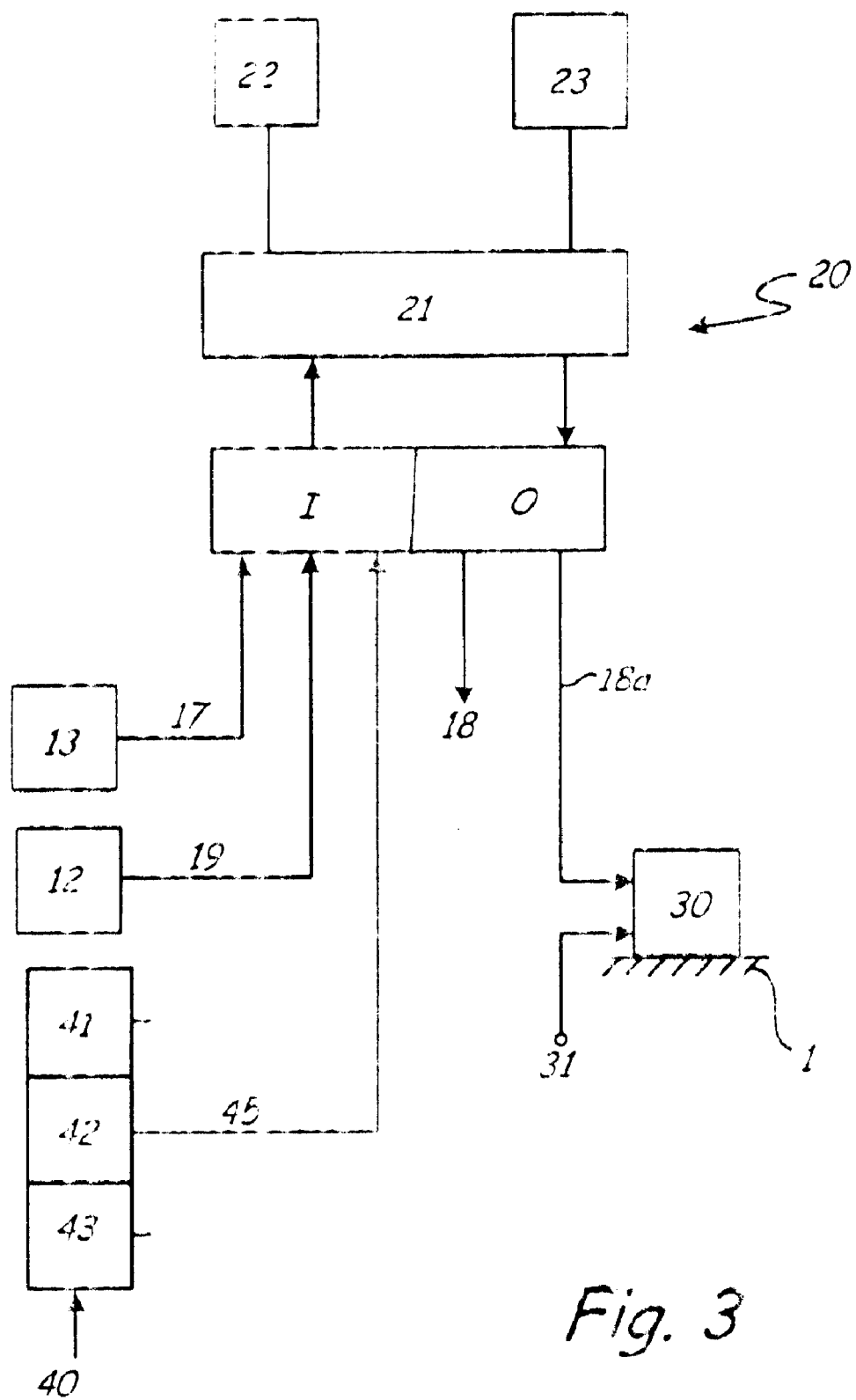
FIG. 3 depicts a schematic wiring diagram, comprising the vibrator motor, an input means, a position sensor and the force sensor.

FIG. 3 shows how the vibrator motor 30 is embedded in the pressure monitoring system and how the drive motor 11 is monitored. The vibrator motor 30 is further connected to an input means 40 via the control system 20. The pressure is monitored by means of the force sensor 13, whose reading signal passes to the control system 20 via the line 17. If the control system 20 determines an occlusion by comparing the force measured by the force sensor 13 with a maximum value, it switches on the vibrator motor 30 via a line 18. The user can manually switch the vibrator motor off via a line 31 by means of the input means 40. If a malfunction of the motor 11 is determined with the aid of the sensor 12, the vibrator motor 30 is likewise switched on by the control system 20. In particular, it switches the vibrator motor 30 on when it switches off the motor 11, as described above. The drive is monitored by means of the impeller and the optical sensor co-operating with the same, which in FIG. 3 are indicated together by the reference numeral 12.

The input means 40 is formed by a keyboard or a touch screen. The individual input appliances of the input means 40, representing other such appliances, are indicated by the reference numerals 41, 42 and 43, which are formed either by keys or keypads. Each of the input appliances of the input means 40 is electrically connected to the input I of the control system 20 via a line 45. Only one line to the control system 20 is shown, as representative of the possible plurality of such lines 45. The control system 20 emits an individual control signal via the connection line 18a, depending on the input appliance of the input means 40 currently being operated, and the vibrator motor 30 generates a characteristic vibrating signal for each of the input appliances, depending on this control signal.

When priming, the threaded rod 7 is driven towards the piston 6, from a starting state in which the ampoule 2 has been inserted into the casing 1 and its sealing membrane at the outlet 3 has been pierced by a connection needle. The motor 11 moves in overdrive, significantly above the start-stop frequency, until it abuts the piston 6. In overdrive, it is operated at a pulse frequency which is preferably at least twice as large as its start-stop frequency. As soon as the threaded rod 7 abuts the piston 6 with its pallet, the motor 11 is automatically cut off since its torque above the start-stop frequency is not sufficient to drive the threaded rod 7 and the piston 6. The stopping position of the motor 11 is registered in the control system 20 and stored as a reference position for delivering the product. If a suitable reference value for a particular position of the piston 6 and the type of ampoule 2 being used is stored in the control system 20, then the control system 20 can ascertain whether the ampoule 2 is a full or for example half-full ampoule from the actual position of the piston as determined when the threaded rod 7 moves up to it, by comparing this with said reference value.

In the exemplary embodiment, the motor 11—formed as a step or stepper motor with a settable start-stop frequency—is automatically re-started, once it has been cut off as described above, such that the piston 6 is then advanced in the ampoule 2. In the course of priming, the piston 6 is advanced in the ampoule 2 towards the outlet 3 until insulin emerges at the delivery point of the infusion needle 5. When the motor 11 is re-started, the vibrator motor 30 is triggered by the control system 20 and thus switched on. Gas bubbles stuck in the fluid guiding system of the device are released by the vibrations of the vibrator motor 30, such that it is ensured that by the end of priming, the fluid guiding system has been thoroughly vented. As soon as it is definitely determined that fluid is emerging, the driven member 7 and therefore also the piston 6 is stopped in the sliding position along the common sliding axis V which it has just reached. It may be stopped manually if the emerging fluid is observed by the user, or also automatically by the control system 20. When it is stopped, in particular by switching off the motor 11, the vibrator motor 30 is simultaneously also stopped or switched off by the control system 20 via the line 18a.

The vibrator motor 30 is then once again ready to receive control signals, for example if an occlusion is determined, or to confirm inputs by means of the input means 40.

In the foregoing description preferred exemplary embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for administering an injectable product in doses, said device comprising:

a casing;

a container for the product, accommodated by the casing;

an appliance for delivering the product from the container, wherein the appliance comprises a piston;

a drive motor for the moving the appliance;

a pressure sensor for monitoring operational pressures associated with the product, wherein the pressure sensor comprises a force sensor that measures a reaction force exerted by the piston; and a vibrator motor associated with the casing, said vibrator motor operably coupled to and triggered by the sensor, such that it vibrates when an operational pressure condition occurs.

2. The device as set forth in claim 1, wherein the force sensor comprises a bending beam with a thin-film strain measuring strip.

3. The device as set forth in claim 1, wherein the casing comprises casing walls and a sliding platform mounted floating on the casing walls in the casing, the reaction force being transferred to the force sensor via the sliding platform.

4. A device for administering an injectable product in doses, said device comprising:

a) a casing;

b) a container for the product, accommodated by the casing;

c) a delivering appliance for delivering the product from the container, wherein the appliance comprises a piston;

d) a drive means for the delivering appliance;

e) a pressure sensor adapted to monitor pressure associated with the product, wherein the pressure sensor comprises a force sensor that measures a reaction force exerted by the piston; and f) and a means for determining a malfunction of the device, wherein g) a vibrator motor is accommodated by the casing, said vibrator motor being triggered by the means for determining a malfunction such that it generates a vibrating alarm signal when a malfunction is determined.

5. The device as set forth in claim 4, wherein the force sensor comprises a bending beam with a thin-film strain measuring strip.

6. The device as set forth in claim 4, wherein the casing comprises casing walls and a sliding platform mounted floating on the casing walls in the casing, the reaction force being transferred to the force sensor via the sliding platform.

7. A device for administering an injectable product in doses, said device comprising:

a) a casing;

b) a container for the product, accommodated by the casing;

c) a delivering anpliance for delivering the product from the container, wherein the appliance comprises a piston;

d) a drive means for the delivering appliance;

e) a pressure monitoring means adapted to monitor pressure associated with the product, wherein the pressure monitoring means comprises a force sensor that measures a reaction force exerted by the piston;

f) and an input means for inputs to the device from a user, wherein g) a vibrator motor is accommodated by the casing;

h) the input means is connected to the vibrator motor; and wherein i) when the input means confirms an input, the vibrator motor is triggered and as confirmation of an input generates a vibrating signal which is characteristic of the input.

8. The device as set forth in claim 7, wherein the force sensor comprises a bending beam with a thin-film strain measuring strip.

9. The device as set forth in claim 7, wherein the casing comprises casing walls and a sliding platform mounted floating on the casing walls in the casing, the reaction force being transferred to the force sensor via the sliding platform.

* * * * *